US012589057B2

(12) United States Patent
Liu et al.

(10) Patent No.: US 12,589,057 B2
(45) Date of Patent: Mar. 31, 2026

(54) COSMETIC COMPOSITION OF LIQUID CRYSTAL LIPID PARTICLES FOR PERSONAL CARE APPLICATIONS

(71) Applicant: BASF SE, Ludwigshafen (DE)

(72) Inventors: Zhao Ting Liu, Shanghai (CN); Yang Zhang, Shanghai (CN); Dong Ryeol Lee, Shanghai (CN); Zhi Rao, Shanghai (CN); Na Zhao, Shanghai (CN)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 17/424,525

(22) PCT Filed: Jan. 27, 2020

(86) PCT No.: PCT/EP2020/051888
§ 371 (c)(1),
(2) Date: Jul. 21, 2021

(87) PCT Pub. No.: WO2020/156983
PCT Pub. Date: Aug. 6, 2020

(65) Prior Publication Data

US 2022/0096337 A1 Mar. 31, 2022

(30) Foreign Application Priority Data

Jan. 30, 2019 (WO) ................ PCT/CN2019/073861
Mar. 6, 2019 (EP) .................................... 19160977

(51) Int. Cl.

| | |
|---|---|
| ***A61K 8/02*** | (2006.01) |
| ***A61K 8/03*** | (2006.01) |
| ***A61K 8/34*** | (2006.01) |
| ***A61K 8/37*** | (2006.01) |
| ***A61K 8/44*** | (2006.01) |
| ***A61K 8/46*** | (2006.01) |
| ***A61K 8/86*** | (2006.01) |
| ***A61Q 17/00*** | (2006.01) |
| ***A61Q 19/00*** | (2006.01) |

(52) U.S. Cl.
CPC .............. *A61K 8/0295* (2013.01); *A61K 8/03* (2013.01); *A61K 8/34* (2013.01); *A61K 8/342* (2013.01); *A61K 8/37* (2013.01); *A61K 8/375* (2013.01); *A61K 8/442* (2013.01); *A61K 8/466* (2013.01); *A61K 8/86* (2013.01); *A61Q 17/00* (2013.01); *A61Q 19/00* (2013.01); *A61K 2800/48* (2013.01)

(58) Field of Classification Search
None
See application file for complete search history.

(56) References Cited

U.S. PATENT DOCUMENTS

| | | | | |
|---|---|---|---|---|
| 5,137,725 | A * | 8/1992 | Handjani | A61Q 17/04 514/963 |
| 2009/0239956 | A1 | 9/2009 | Sakanishi | |
| 2012/0282357 | A1 | 11/2012 | Kuroda et al. | |
| 2013/0259922 | A1* | 10/2013 | Haas | A61P 35/00 264/4.6 |
| 2014/0348759 | A1 | 11/2014 | Hawkins et al. | |
| 2017/0105909 | A1 | 4/2017 | Miyahara et al. | |
| 2017/0157015 | A1* | 6/2017 | Turovets | A61Q 19/08 |
| 2018/0140528 | A1 | 5/2018 | Lee et al. | |
| 2022/0096337 | A1 | 3/2022 | Liu et al. | |

FOREIGN PATENT DOCUMENTS

| | | | |
|---|---|---|---|
| CA | 2 656 928 | | 2/2008 |
| CA | 2 807 386 | | 2/2012 |
| CN | 1420756 | A | 5/2003 |
| EP | 1264632 | A1 | 12/2002 |
| FR | 2597345 | A1 | 10/1987 |
| FR | 2961689 | A1 | 12/2011 |
| JP | 2010-500322 | | 1/2010 |
| JP | 2011-195527 | | 10/2011 |
| JP | 2013-534218 | | 9/2013 |
| JP | 2016-014011 | | 1/2016 |
| JP | 2017-505317 | | 2/2017 |
| JP | 2022-523706 | A | 4/2022 |
| KR | 2016-0141367 | A | 12/2016 |
| KR | 10-2017-0008728 | A | 1/2017 |
| WO | WO-92/04010 | A1 | 3/1992 |
| WO | WO-95/03787 | A1 | 2/1995 |
| WO | 01/34100 | A1 | 5/2001 |
| WO | WO-2005/108383 | A2 | 11/2005 |
| WO | WO-2010/052093 | A1 | 5/2010 |
| WO | 2015/117841 | | 8/2015 |
| WO | WO-2016/003118 | A1 | 1/2016 |
| WO | WO-2017/155156 | A1 | 9/2017 |
| WO | WO-2018/215136 | A1 | 11/2018 |

OTHER PUBLICATIONS

Chen et al., Liposome-induced morphological differentiation of murine neuroblastoma, Nature vol. 263 Oct. 14, 1976, p. 604-606 (Year: 1976).*
Perez et al., Synthesis and characterization of O-acylated-x-hydroxy fatty acids as skin-protecting barrier lipids, Journal of Colloid and Interface Science 490 (2017) 137-146 (Year: 2017).*
European Search Report for EP Patent Application No. 19160977.5, Issued on May 22, 2019, 5 pages.
Mitchell, et al., "Phase behaviour of polyoxyethylene surfactants with water. Mesophase structures and partial miscibility (cloud points)", Journal of the Chemical Society, Faraday Transactions 1: Physical Chemistry in Condensed Phases, vol. 79, Issue 4, 1983, pp. 975-1000.

(Continued)

*Primary Examiner* — Jennifer A Berrios
(74) *Attorney, Agent, or Firm* — Baltazar Gomez

(57) ABSTRACT

The presently claimed invention relates to liquid crystal lipid particles. The presently claimed invention relates to liquid crystal lipid particles which are used in topical composition which has high moisturization efficacy, excellent skin feel, skin softness, and skin smoothness benefits.

16 Claims, 5 Drawing Sheets

(56) References Cited

OTHER PUBLICATIONS

International Application No. PCT/EP2020/051888, International Search Report and Written Opinion, mailed Apr. 6, 2020.
International Application No. PCT/EP2020/051888, International Preliminary Report on Patentability, mailed Apr. 26, 2021.
Wang Xuemei, "[Is my Look Fashionable or Not]", Cosmetics and Health & Beauty, Anhui University Press, Sep. 2004, p. 54, with English translation.
Office Action received for Australian Patent Application No. 2020215227, mailed on Sep. 26, 2024, 3 pages.
Office Action received for Japanese Patent Application No. 2021-544120, mailed on Aug. 5, 2024, 10 pages with English translation.
Office Action issued in Malaysian Patent Application No. PI2021004269 on Jan. 20, 2025, 4 pages.
Office Action issued in Chinese Patent Application No. 202080011470.1 on Jan. 13, 2025, 4 pages (with English translation).
Office Action received for Chinese Patent Application No. 202080011470.1, mailed on Oct. 30, 2024, 10 pages with English translation.
Office Action received for Indonesian Patent Application No. P00202105691, mailed on Feb. 27, 2025, 6 pages with English translation.
Office Action received for Brazilian Patent Application No. BR112021014869-8, mailed on Jan. 24, 2025, 6 pages with Partial English Translation.
Office Action received for Korean Patent Application No. 10-2021-7026918, mailed on Feb. 11, 2025, 20 pages with English Translation.
Office Action issued for European Patent Application No. 20 702 274.0 on Oct. 8, 2024, 13 pages.
Patrick J. Sinko, "Chapter 16: Colloidal Dispersions" Martin's physical pharmacy and pharmaceutical sciences, 6th Edition, Feb. 2010, pp. 386-409.

* cited by examiner

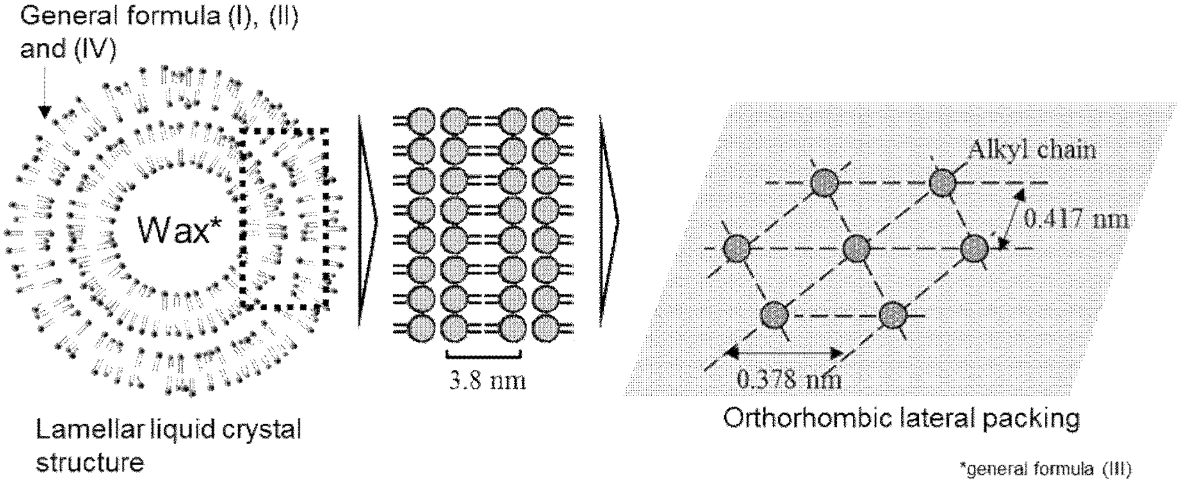
Figure 1: Orthorhombic lateral packing of the liquid crystal lipid particles

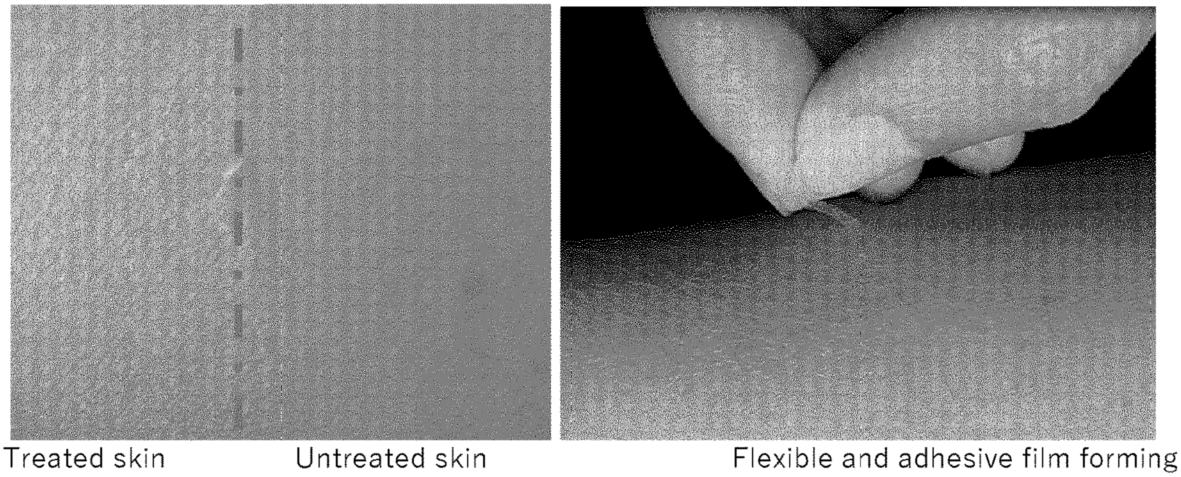
Treated skin Untreated skin Flexible and adhesive film forming
Figure 2 showing the transparent/flexible lipid film formed by treating of the liquid crystal lipid particle

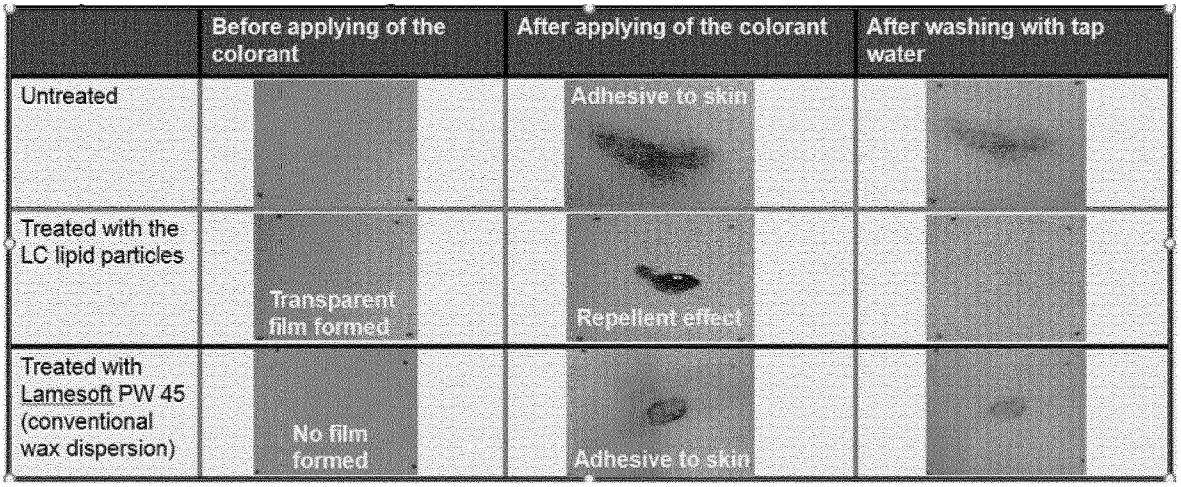
Figure 3: Film formed by the liquid crystal lipid particles has a repellent effect

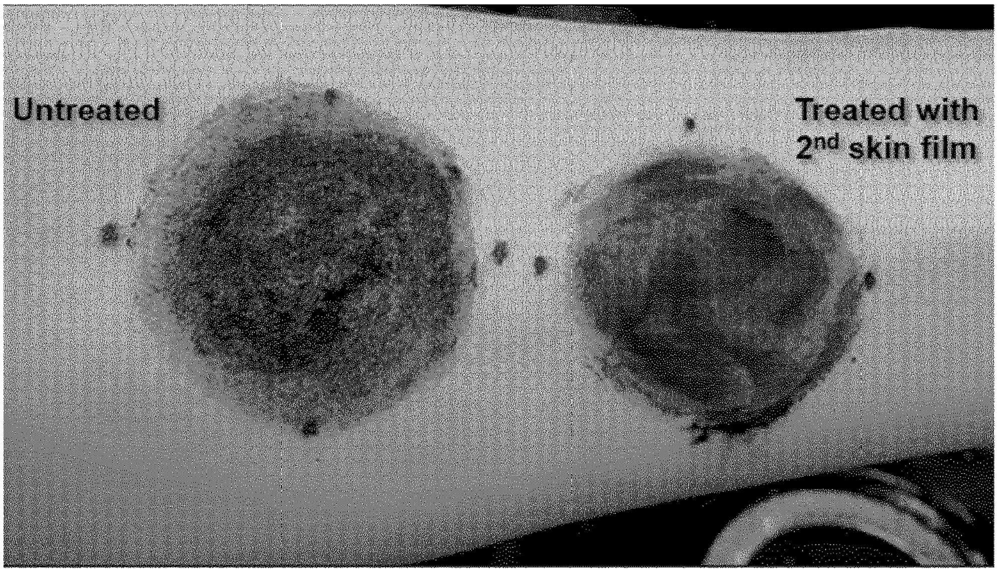
Application of the colorant as a pollutant before rinsing
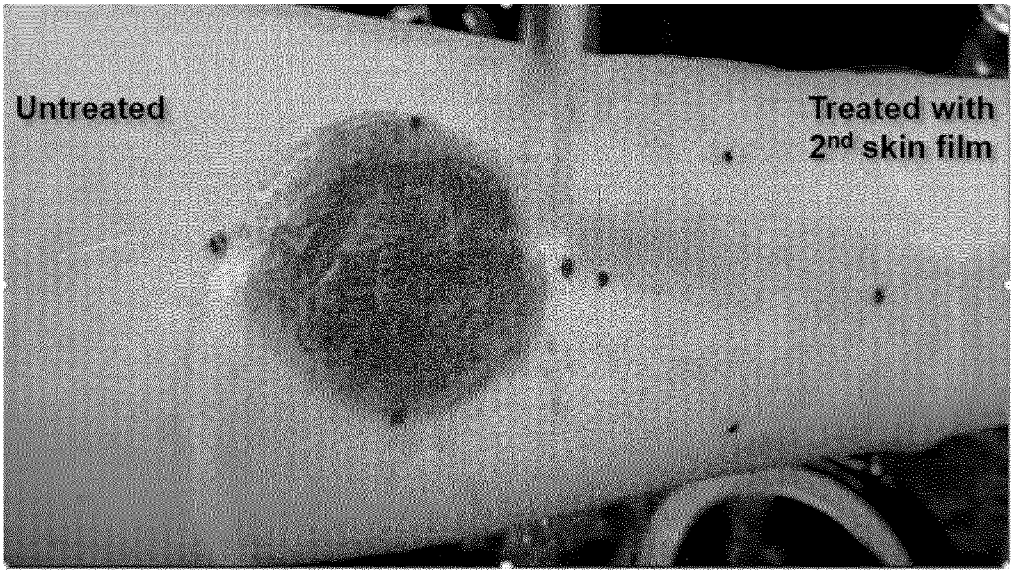
After rinsing with water- colorant is removed
Figure 4: Film formed by the liquid crystal lipid particles has an anti- adhesion effect to the pollutant Increase in the moisturizing effect of the composition comprising liquid crystal lipid particle when measured on the Corneometer. 4T4 (■), 4T5 (■)

COSMETIC COMPOSITION OF LIQUID CRYSTAL LIPID PARTICLES FOR PERSONAL CARE APPLICATIONS

CROSS-REFERENCE TO RELATED APPLICATIONS

This is the U.S. national phase of International Application No. PCT/EP2020/051888, filed Jan. 27, 2020, which claims the benefit of PCT/CN2019/073861, filed Jan. 30, 2019, and European Patent Application No. 19160977.5, filed on Mar. 6, 2019, and.

FIELD OF THE INVENTION

The presently claimed invention relates to liquid crystal lipid particles. In particular, the presently claimed invention relates to liquid crystal lipid particles which are used in topical compositions. The topical composition containing the liquid crystal lipid composition has a high moisturization efficacy, an excellent skin feel, a skin softness, and a skin smoothness benefits.

BACKGROUND OF THE INVENTION

Skin plays a very important role as a barrier film which prevents any loss of biologically essential components such as water while simultaneously serving for a protection from any biological, chemical or physical invasion of external microorganisms, chemicals, ultraviolet light and the like. The part functioning as a barrier film is a horny cell layer, the stratum corneum, whose thickness is about 20 μm and which is located in the outermost layer of the skin and forms a tough barrier film in a structure of the corneocyte stacked as bricks binding to each other via intercellular lipids serving as a mortar.

The stratum corneum serves important barrier function, foremost of which is preventing excessive transepidermal water loss ("TEWL"). In addition to retarding TEWL, the sheets of the lipid lamellar membranes also protect against ingress of foreign chemicals and microorganisms.

Emulsifiers that form lamellar liquid crystals are marketed by cosmetic ingredient suppliers as mimicking the multi-lamellar lipid structure of the stratum corneum In the area of cosmetics, it is believed that the smaller particles are readily absorbed into the skin and repair damage easily and more efficiently. Incorporation of nanotechnology in cosmeceuticals is aimed at making the incense of perfumes last longer, sunscreens to protect the skin, antiaging creams to fight back the years, and moisturizers to maintain the hydration of skin. Some of the nanotechnology-based innovations are nanoemulsions (which are transparent and have unique tactile and texture properties), nanocapsules (which are used in skin care products), nanopigments (that are transparent and increase the efficiency of sunscreen products), liposome formulations (which contain small vesicles consisting of conventional cosmetic materials that protect oxygen or light sensitive cosmetic ingredients), niosomes, nanocrystals, solid lipid nanoparticles, carbon nanotubes, fullerenes, and dendrimers. The primary advantages of using nanoparticles in cosmeceuticals include improvement in the stability of cosmetic ingredients (e.g., vitamins, unsaturated fatty acids, and antioxidants) by encapsulating within the nanoparticles; efficient protection of the skin from harmful ultraviolet (UV) rays; aesthetically pleasing products (e.g., in mineral sunscreens, using smaller particles of active mineral allows them to be applied without leaving a noticeable white cast); targeting of active ingredient to the desired site and controlled release of active ingredients for a prolonged effect.

WO 2005/108383 A1 discloses oil-in-water emulsions comprising a mixture of at least two sucrose esters in combination with at least one solid fatty alcohol which forms a multi-lamellar liquid crystalline network that effectively moisturizes and protects the skin, and provides a useful vehicle for delivery of an active ingredients.

US 2009/0239956 A1 relates to lamellar liquid crystal compositions for cosmetic use which contain one or more polyglycerol monoethers each having a specific structure, and which are used to remove makeup and cosmetics containing the cosmetic compositions.

US 2012/0282357 A1 discloses a method for adjusting the amount of calcium ions in the epidermis, comprising applying a material for enhancing the skin barrier function to the skin of a subject, wherein the material is selected from the group consisting of Pimpinella extract, Asteroidea extract, L-Carnitine, Royal jelly hydrolysate, α,ε-bis(γ-N-lauroyl-glutamyl)lysine, *Palmaria* extract, ε,γ-Glutamyl lysine, *Coptis japonica* extract and citrus aurantium peel extract.

WO 2016/003118 A1 relates to a multi-phase cosmetic composition comprising cholesterol liquid crystals resulting in an improvement in the use feeling.

While efforts have been going on for enhancing the skin barrier function by using several methods like natural extracts formulated in skin creams, lotions etc., these extracts are efficient to enhance the skin barrier function biologically, but they do not lead to an enhancement of the physical barrier function.

Thus, there remains a need to effectively improve the skin barrier function by enhancing the skin's own ability to maintain and/or repair the strength of its barrier, so that the protective barrier formed is completely natural. Further there exists a need to also have a skin composition which exhibits enhanced skin protection properties and enhanced skin moisturization.

SUMMARY OF THE INVENTION

Surprisingly, it was found that the liquid crystal lipid particles of the presently claimed invention are effective in improving the barrier function and protecting the skin from harmful pollutants and also enhance the skin moisturizing effect.

Liquid crystal lipid particles are another type of system which offers the dual advantage of a liquid phase and solid phase. These particles can be easily manufactured and offer several advantages.

Hence, in one aspect, the presently claimed invention relates to the method for reducing the adhesion of dust to skin comprising applying to the skin at least one liquid crystal lipid particle, wherein the liquid crystal lipid particles comprises compounds represented by the general formulae (I) to (VI), comprising, at least one compound of formula (I)

general formula (I)

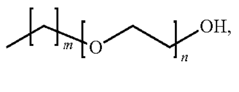

wherein m is an in the range from ≥10 to ≤24 and n is an integer in the range from ≥1 to ≤25, at least one compound of formula (II)

general formula (II)

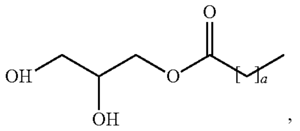

wherein a is an in the range from ≥10 to ≤24, at least one compound of formula (III)

general formula (III)

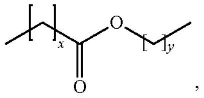

wherein x is an in the range from ≥10 to ≤24 and y is an integer in the range from ≥10 to ≤25, at least one compound of formula (IV)

general formula (IV)

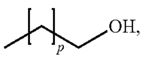

wherein p is an in the range from ≥10 to ≤16, at least one compound of formula (V)

general formula (V)

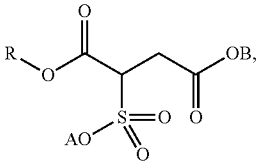

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

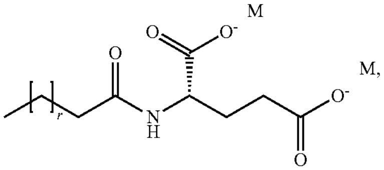

wherein r is an in the range from ≥9 to ≤18, and M is a hydrogen atom, an alkali earth metal or an alkaline earth metal.

In yet another aspect the presently claimed invention is directed to the use of at least one liquid crystal lipid particle for reducing the adhesion of dust to the skin, wherein the liquid crystal lipid particles comprise compounds represented by the general formulae (I) to (VI), comprising, at least one compound of formula (I)

general formula (I)

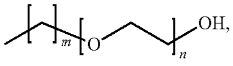

wherein m is an in the range from ≥10 to ≤24 and n is an integer in the range from ≥1 to ≤25, at least one compound of formula (II)

general formula (II)

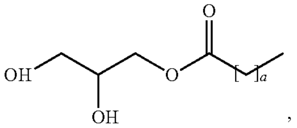

wherein a is an in the range from ≥10 to ≤24, at least one compound of formula (III)

general formula (III)

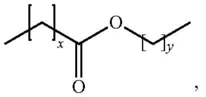

wherein x is an in the range from ≥10 to ≤24 and y is an integer in the range from ≥10 to ≤25, at least one compound of formula (IV)

general formula (IV)

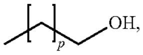

wherein p is an in the range from ≥10 to ≤16, at least one compound of formula (V)

general formula (V)

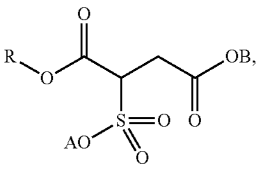

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

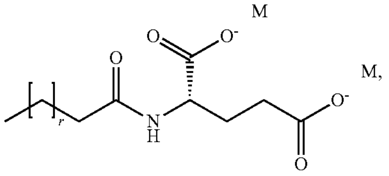

wherein r is an in the range from ≥9 to ≤18, and M is a hydrogen atom, an alkali earth metal or an alkaline earth metal.

Another aspect of the presently claimed invention related to a topical composition comprising, at least one liquid crystal particle as described herein above and below, at least one thickening agent and water.

BRIEF DESCRIPTION OF THE FIGURES

FIG. 1: Orthorhombic lateral packing of the liquid crystal lipid particles

FIG. 2: Figure showing the transparent/flexible lipid film formed by treating of the liquid crystal lipid particles FIG. 3: Film formed by the liquid crystal lipid particles has a repellent effect FIG. 4: Film formed by the liquid crystal lipid particles has an anti-adhesion effect

DETAILED DESCRIPTION OF THE INVENTION

Figure 5:
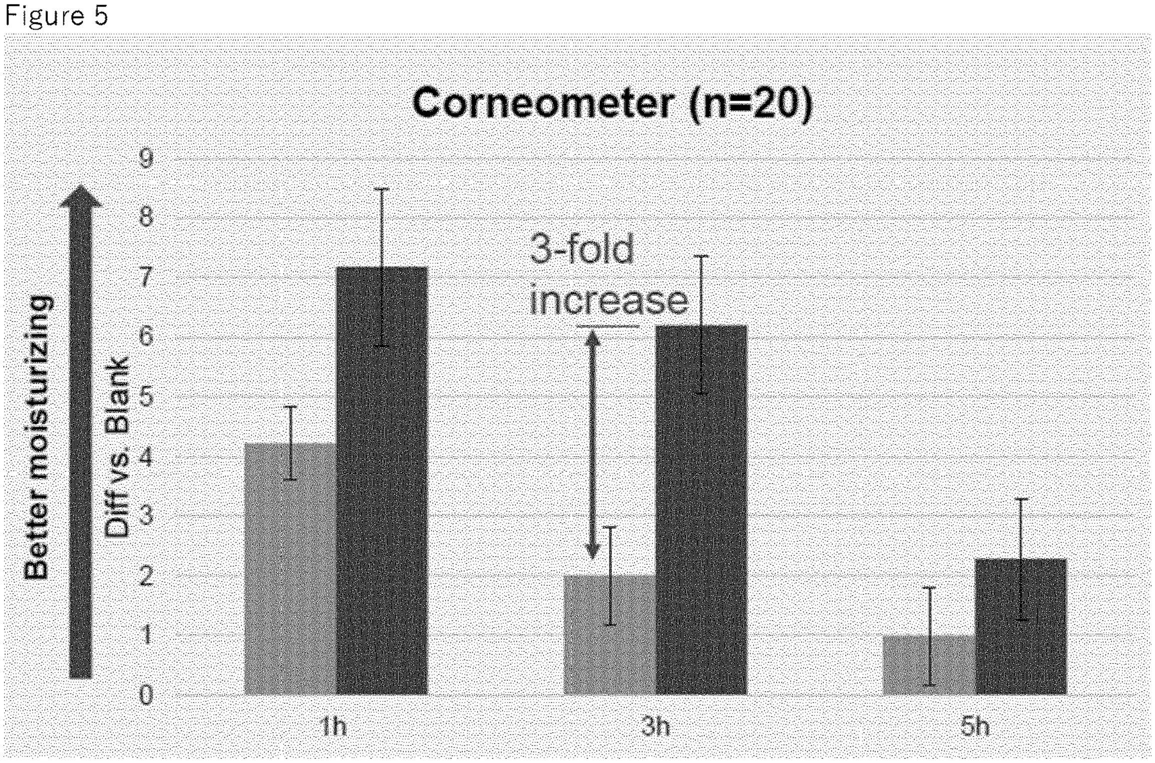
FIG. 5: Increase in the moisturizing effect of the composition comprising liquid crystal lipid particles when measured on the corneometer

Before the present compositions and formulations of the presently claimed invention are described, it is to be understood that this invention is not limited to particular compositions and formulations described, since such compositions and formulation may, of course, vary.

It is also to be understood that the terminology used herein is not intended to be limiting, since the scope of the presently claimed invention will be limited only by the appended claims.

If hereinafter a group is defined to comprise at least a certain number of embodiments, this is meant to also encompass a group which preferably consists of these embodiments only. Furthermore, the terms 'first', 'second', 'third' or 'a', 'b', 'c', etc. and the like in the description and in the claims, are used for distinguishing between similar elements and not necessarily for describing a sequential or chronological order. It is to be understood that the terms so used are interchangeable under appropriate circumstances and that the embodiments of the presently claimed invention described herein are capable of operation in other sequences than described or illustrated herein. In case the terms 'first', 'second', 'third' or '(A)', '(B)' and '(C)' or '(a)', '(d)', 'H' etc. relate to steps of a method or use or assay there is no time or time interval coherence between the steps, that is, the steps may be carried out simultaneously or there may be time intervals of seconds, minutes, hours, days, weeks, months or even years between such steps, unless otherwise indicated in the application as set forth herein above or below.

Furthermore, the ranges defined throughout the specification include the end values as well i.e. a range of 1 to 10 implies that both 1 and 10 are included in the range. For the avoidance of doubt, applicant shall be entitled to any equivalents according to applicable law.

In the following passages, different aspects of the presently claimed invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to 'one embodiment' or 'an embodiment' means that a particular feature, structure or characteristic described in connection with the embodiment is included in at least one embodiment of the presently claimed invention. Thus, appearances of the phrases 'in one embodiment' or 'in an embodiment' in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the presently claimed invention, and form different embodiments, as would be understood by those in the art. For example, in the appended claims, any of the claimed embodiments can be used in any combination "Topical application" means to apply or spread a composition directly onto the surface of the skin of a human or animal body, preferably onto the face, scalp, feet, limbs or trunk.

The presently claimed invention relates to a method for reducing the adhesion of dust to skin comprising applying to the skin at least one liquid crystal lipid particle wherein the liquid crystal lipid particles comprises compounds represented by the general formulae (I) to (VI), comprising, at least one compound of formula (I)

general formula (I)

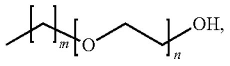

wherein m is an in the range from ≥10 to ≤24 and n is an integer in the range from ≥1 to ≤25, at least one compound of formula (II)

general formula (II)

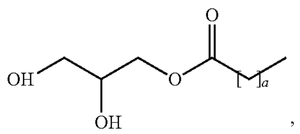

wherein a is an in the range from ≥10 to ≤24, at least one compound of formula (III)

general formula (III)

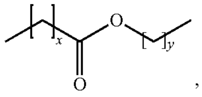

, wherein x is an in the range from ≥10 to ≤24 and y is an integer in the range from ≥10 to ≤25, at least one compound of formula (IV)

general formula (IV)

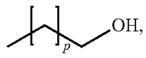

wherein p is an in the range from ≥10 to ≤16, at least one compound of formula (V)

general formula (V)

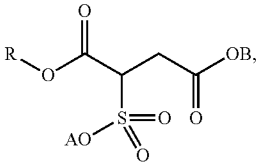

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

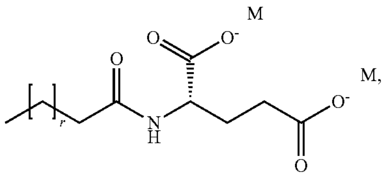

wherein r is an in the range from ≥9 to ≤18, and M is a hydrogen atom, an alkali earth metal or an alkaline earth metal.

In an embodiment, the presently claimed invention is directed to the use of at least one liquid crystal lipid particle for reducing the adhesion of dust to the skin, wherein the liquid crystal lipid particles comprise compounds represented by the general formulae (I) to (VI), comprising, at least one compound of formula (I)

general formula (I)

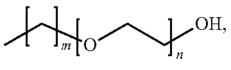

wherein m is an in the range from ≥10 to ≤24 and n is an integer in the range from ≥1 to ≤25, at least one compound of formula (II)

general formula (II)

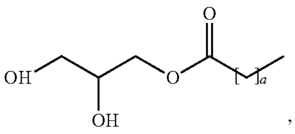

, wherein a is an in the range from ≥10 to ≤24, at least one compound of formula (III)

general formula (III)

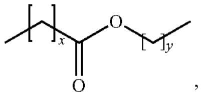

, wherein x is an in the range from ≥10 to ≤24 and y is an integer in the range from ≥10 to ≤25, at least one compound of formula (IV)

general formula (IV)

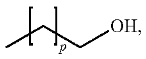

wherein p is an in the range from ≥10 to ≤16, at least one compound of formula (V)

general formula (V)

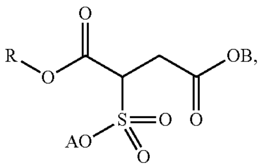

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

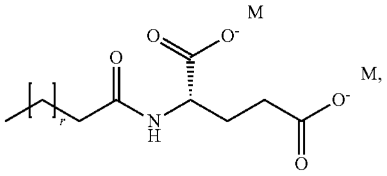

wherein r is an in the range from ≥9 to ≤18, and M is a hydrogen atom, an alkali earth metal or an alkaline earth metal.

In an embodiment of the present invention, the topical composition comprises at least one liquid crystal particle as defined above, at least one thickening agent and water.

The liquid crystal lipid particles of the presently claimed invention comprises at least one compound selected from the group consisting of compounds represented by the general formulae (I) to (IV), general formula (I)

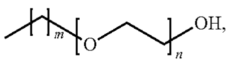

wherein m is an in the range from ≥10 to ≤24 and n is an integer in the range from ≥1 to ≤25, general formula (II)

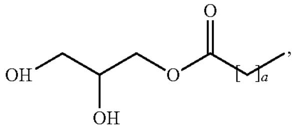

wherein a is an in the range from ≥10 to ≤24, general formula (III)

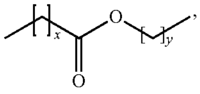

wherein x is an in the range from ≥10 to ≤24 and y is an integer in the range from ≥10 to ≤25, and general formula (IV)

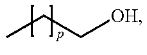

wherein p is an in the range from ≥10 to ≤16.

The liquid crystal particles of the presently claimed invention comprises at least one compound selected from the group consisting of compounds represented by the general formula (I) to (IV) and, in addition, at least one compound of general formula (V) or (VI)

general formula (V)

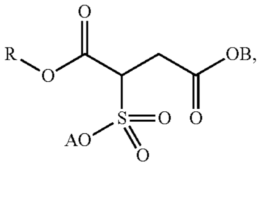

wherein A and B are each independently a hydrogen atom or alkali earth metal or an alkaline earth metal, and R is a linear or branched, saturated or unsaturated $C_{10}$-$C_{20}$ aliphatic radical.

general formula (VI)

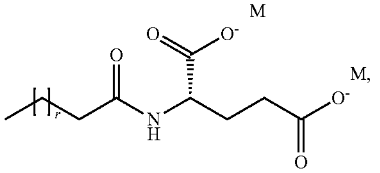

wherein r is an in the range from ≥9 to ≤18, and M is a hydrogen atom, an alkali earth metal or an alkaline earth metal.

In an embodiment of the presently claimed invention, the liquid crystal lipid particles comprises at least one compound represented by the general formula (I) and at least one compound selected from the group consisting of compounds represented by the general formulae (II), (III) and (IV).

In an embodiment of the presently claimed invention, the liquid crystal lipid particles comprise at least one compound represented by the general formula (I) and at least one compound selected from the group consisting of compounds represented by the general formulae (II), (III) (IV), (V), and (VI).

In yet another embodiment of the presently claimed invention, the liquid crystal lipid particles comprise at least one compound represented by the general formula (II) and at least one compound selected from the group consisting of compounds represented by the general formulae (I), (III) and (IV).

In yet another embodiment of the presently claimed invention, the liquid crystal lipid particles comprise at least one compound represented by the general formula (II) and at least one compound selected from the group consisting of compounds represented by the general formulae (I), (III), (IV), (V) and (VI).

In yet another embodiment of the presently claimed invention, the liquid crystal lipid particles comprise at least one compound represented by the general formula (III) and at least one compound selected from the group consisting of compounds represented by the general formulae (I), (II) and (IV).

In yet another embodiment of the presently claimed invention, the liquid crystal lipid particles comprise at least one compound represented by the general formula (III) and at least one compound selected from the group consisting of compounds represented by the general formulae (I), (II), (IV), (V) and (VI).

In yet another embodiment of the presently claimed invention, the liquid crystal lipid particles comprise at least one compound represented by the general formula (IV) and at least one compound selected from the group consisting of compounds represented by the general formulae (I), (II), (III), (V) and (VI).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV).

In another embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (V).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (VI).

In a further embodiment of the presently claimed invention, the liquid crystal lipid particles comprise at least one compound represented by the general formula (I) and at least one compound represented by the general formula (II) and at least one compound represented by the general formula (III) and at least one compound represented by the general formula (IV) and at least one compound represented by the general formula (VI) and at least one compound represented by the general formula (V). and at least one compound represented by the general formula (VI).

In an embodiment of the presently claimed invention, the liquid crystal lipid particles comprise at least one compound represented by the general formula (I)

general formula (I)

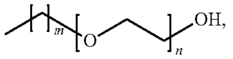

wherein m is an in the range from ≥10 to ≤24 and n is an integer in the range from ≥1 to ≤25.

In an embodiment of the presently claimed invention, the at least one compound of general formula (I) is selected from the group consisting of ceteareths, polyoxyethylene stearyl ether, and polyoxyethylene cetyl ether.

In an embodiment of the presently claimed invention, the at least one compound of general formula (I) is selected from the group consisting of ceteareth-12, ceteareth-12, ceteareth-30.

In a most preferred embodiment of the presently claimed invention, the at least one compound of general formula (I) is selected from the group consisting of ceteareth-12, ceteareth-12.

In an embodiment of the presently claimed invention, in the at least one compound of general formula (II)

general formula (II)

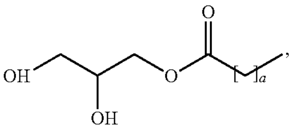

a is an in the range from ≥10 to ≤24,

In an embodiment of the presently claimed invention, the at least one compound of general formula (II) is selected from the group consisting of glycerol stearate, glycerol laurate and glycerol palmitate, glycerol caprylate, glycerol myristate.

In a preferred embodiment of the presently claimed invention, the at least one compound of general formula (II) is glycerol stearate.

In an embodiment of the presently claimed invention, in the at least one compound of general formula (III), general formula (III)

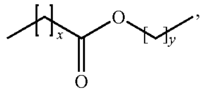

x is an in the range from ≥10 to ≤24 and y is an integer in the range from ≥10 to ≤25, In an embodiment of the presently claimed invention, the at least one compound of general formula (III) is selected from the group consisting of myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate.

In a further embodiment of the presently claimed invention, the at least one compound of general formula (III) is selected from the group consisting of cetyl palmitate, myristyl myristate, tetra decyl tetra decanoate, and behenyl behenate.

In a preferred embodiment of the presently claimed invention, the at least one compound of general formula (III) is selected from the group consisting of cetyl palmitate, myristyl myristate.

In an embodiment of the presently claimed invention, in the at least one compound of general formula (IV), general formula (IV)

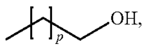

p is an in the range from ≥10 to ≤16.

In yet another embodiment of the presently claimed invention, the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol and stearyl alcohol or mixtures thereof.

In a preferred embodiment of the presently claimed invention, the at least one compound of general formula (IV) is selected from the group consisting of lauryl alcohol, myristyl alcohol, cetyl alcohol, stearyl alcohol or mixtures thereof.

In a most preferred embodiment of the presently claimed invention, the at least one compound of general formula (IV) is a mixture of cetyl alcohol and stearyl alcohol.

In an embodiment of the presently claimed invention, in the at least one compound of general formula (V), general formula (V)

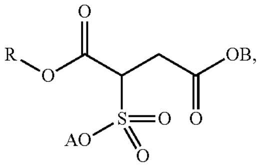

A and B are each independently a hydrogen atom or alkali earth metal or an alkaline earth metal, and R is a linear or branched, saturated or unsaturated $C_{10}$-$C_{20}$ aliphatic radical.

In an embodiment of the presently claimed invention, in the at least one compound of general formula (V), A and B are each independently an alkali earth metal, and R is a linear or branched, saturated or unsaturated $C_{10}$-$C_{20}$ aliphatic radical.

In a further embodiment of the presently claimed invention, in the at least one compound of general formula (V), the R is n-decyl, iso-decyl, n-undecyl, iso-undecyl, n-dodecyl, isododecyl, n-tridecyl, iso-tridecyl, n-tetradecyl, iso-tetradecyl, n-pentadecyl, iso-pentadecyl, n-hexadecyl, iso-hexadecyl, n-heptadecyl, iso-heptadecyl, n-octadecyl, iso-octadecyl and n-octadecenyl.

In a further embodiment of the presently claimed invention, the at least one compound of general formula (V) is disodium $C_{10}$-$C_{18}$ alkyl sulfosuccinate.

In a preferred embodiment of the presently claimed invention, the at least one compound of general formula (V) is disodium $C_{12}$-$C_{18}$ alkyl sulfosuccinate In a most preferred embodiment of the presently claimed invention, the at least one compound of general formula (V) is $C_{16}$-$C_{18}$ alkyl sulfosuccinate.

In an embodiment of the presently claimed invention, in the at least one compound of general formula (VI), general formula (VI)

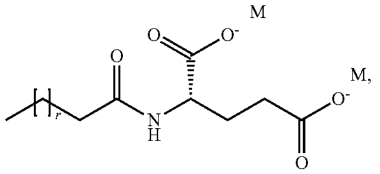

r is an in the range from ≥9 to ≤18, and M is a hydrogen atom, an alkali earth metal or an alkaline earth metal.

In an embodiment of the presently claimed invention, in the at least one compound of general formula (VI), M is sodium or potassium and r is an in the range from ≥9 to ≤18

In an embodiment of the presently claimed invention, the at least one compound of general formula (VI) is selected from the group consisting of sodium stearoyl glutamate, sodium lauroyl glutamate, sodium cocoyl glutamate, sodium myristoyl glutamate, potassium cocoyl glutamate, potassium lauroyl glutamate, and combinations thereof.

In an embodiment of the presently claimed invention, the at least one compound of general formula (VI) is selected from the group consisting of sodium lauroyl glutamate, sodium cocoyl glutamate, sodium myristoyl glutamate and sodium stearoyl glutamate.

In an embodiment of the presently claimed invention the crystal lipid particles comprise ceteareths, glycerol stearate, cetyl palmitate, cetyl alcohol and stearyl alcohol.

In yet another embodiment of the presently claimed invention, the liquid crystal lipid particles comprise ceteareths, glycerol stearate, cetyl palmitate, myristyl myristate, cetyl alcohol and stearyl alcohol.

In a further embodiment of the presently claimed invention, the liquid crystal lipid particles comprise ceteareths, glycerol stearate, cetyl palmitate, myristyl myristate, cetyl alcohol, stearyl alcohol and a compound selected from the group of disodium $C_{10}$-$C_{18}$ alkyl sulfosuccinate and sodium stearoyl glutamate.

In a preferred embodiment of the presently claimed invention, the liquid crystal lipid particles comprise ceteareth-12, ceteareth-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium lauroyl glutamate In another preferred embodiment of the presently claimed invention, the liquid crystal lipid particles comprise ceteareth-12, ceteareth-12, glycerol stearate, cetyl palmitate, myristyl myristate, cetyl alcohol, stearyl alcohol and a compound selected from the group of disodium $C_{12}$-$C_{14}$ alkyl sulfosuccinate and sodium lauroyl glutamate In yet another preferred embodiment of the presently claimed invention, the liquid crystal lipid particles comprise ceteareth-12, ceteareth-12, glycerol stearate, cetyl palmitate, myristyl myristate, cetyl alcohol, stearyl alcohol and a compound selected from the group of disodium $C_{12}$-$C_{14}$ alkyl sulfosuccinate and sodium stearoyl glutamate.

In a most preferred embodiment of the presently claimed invention, the liquid crystal lipid particles comprise ceteareth-12, ceteareth-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium stearoyl glutamate.

In an embodiment of the presently claimed invention, the liquid crystal lipid particles have an average particle size of ≥20 nm to ≤500 nm, determined using dynamic light scattering using Malvern DLS ZS90.

In an embodiment of the presently claimed invention, the liquid crystal lipid particles have an average particle size of ≥20 nm to ≤300 nm, determined using dynamic light scattering using Malvern DLS ZS90.

In an embodiment of the presently claimed invention, the liquid crystal lipid particles have an average particle size of ≥20 nm to ≤150 nm, determined using dynamic light scattering using Malvern DLS ZS90.

In an embodiment of the presently claimed invention, the liquid crystal lipid particles have an average particle size of 20 nm, 30 nm, 40 nm, 50 nm, 60 nm, 70 nm, 80 nm, 90 nm, 100 nm, 110 nm, 120 nm, 130 nm, 140 nm or 150 nm, determined using dynamic light scattering using Malvern DLS ZS90.

Zeta potential of the liquid crystal lipid particles is a measure of the charge on the surface of the particles and is a measure of the stability of the lipid particles. The higher the zeta potential higher is the stability, In an embodiment of the presently claimed invention, the liquid crystal lipid particles have a zeta potential of more than 20 mV, when measured at 40° C.

In an embodiment of the presently claimed invention, the liquid crystal lipid particles have a zeta potential of more than 30 mV, when measured at 40° C.

In an embodiment of the presently claimed invention, the liquid crystal lipid particles are prepared by using the phase inversion temperature method.

In a further embodiment of the presently claimed invention, the liquid crystal lipid particles are prepared using the phase inversion temperature method as disclosed in D. J. Mitchell et al. Phase behavior of polyoxyethylene surfactants with water. Mesophase structures and partial miscibility (cloud points), J. Chem. Soc. Farayday Trans., 79, 975-1000 (1983) incorporated herein by reference.

In an embodiment of the presently claimed invention, the liquid crystal lipid particles have an orthorhombic lateral packing.

In an embodiment of the presently claimed invention, the liquid crystal lipid particles are included in a topical composition for application to the skin.

In an embodiment of the presently claimed invention, the liquid crystal lipid particles form the base in any topical composition for application to the skin.

In an embodiment of the presently claimed invention, the at least one liquid crystal lipid particle is present in an amount in the range of ≥1% to ≤30% by weight, based on the total weight of the topical composition.

In a further embodiment of the presently claimed invention, the at least one liquid crystal lipid particle is present in an amount in the range of ≥1% to ≤25% by weight, based on the total weight of the topical composition.

In a preferred embodiment of the presently claimed invention, the at least one liquid crystal lipid particle is present in an amount in the range of ≥1% to ≤20% by weight, based on the total weight of the topical composition.

In a most preferred embodiment of the presently claimed invention, the at least one liquid crystal lipid particle is present in an amount in the range of ≥1% to ≤15% by weight, based on the total weight of the topical composition.

In an embodiment of the presently claimed invention, the topical composition is present in the form of a cream, a foam, a lotion, a gel, a paste, a spray, a patch, a spray patch, a mousse or an ointment.

In an embodiment of the presently claimed invention, the topical composition further comprises at least one auxiliary agent selected form the group consisting of anti-wrinkle active agents, anti-acne active agents, emulsifiers, antioxidants, emollients, self-tanning active agents, skin lightening agents, sunscreen agents, UV absorbing agents, thickening agents, humectants, abrasives, absorbents, fragrances, buffering agents, opacifying agents, colorants, preservatives, fillers, pH adjusting agents and solvents.

In an embodiment of the presently claimed invention, the active agents are selected from the group consisting of anti-wrinkle agents like retinol, hyaluronic acid, ceramides, niacinamide, vitamin E, alpha hydroxy acids, anti-acne agents like clindamycin, benzamycin, benzoyl peroxide, and isotretinoin.

In an embodiment of the presently claimed invention, the skin lightening agents are selected from the group consisting of tretinoin, hydroquinone, resorcinol, arbutin, kojic acid, azelaic acid, vitamin C, glutathione and alpha hydroxy acids.

In an embodiment of the presently claimed invention, the UV absorbing agents or sun screen agents are selected from the group consisting of suitable sunscreening agents including, for example: p-aminobenzoic acid, its salts and its derivatives (ethyl, isobutyl, glyceryl esters; p-dimethylaminobenzoic acid, diethylaminohydroxybenzoylhexyl benzoate); anthranilates (i.e., o-aminobenzoates; methyl, menthyl, phenyl, benzyl, phenylethyl, linalyl, terpinyl, and cyclohexenyl esters); salicylates (amyl, phenyl, benzyl, menthyl, glyceryl, and dipropyleneglycol esters); cinnamic acid derivatives (menthyl and benzyl esters, butyl cinnamoyl pyruvate); dihydroxycinnamic acid derivatives (umbelliferone, methylumbelliferone, methylaceto-umbelliferone); trihydroxy-cinnamic acid derivatives (esculetin, methylesculetin, daphnetin, and the glucosides, esculin and daphnin); hydrocarbons (diphenylbutadiene, stilbene); dibenzalacetone and benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxybiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); hydroxy- or methoxy-substituted benzophenones; uric and vilouric acids; tannic acid and its derivatives (e.g., hexaethylether); (butyl carbotol) (6-propyl piperonyl) ether; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; and 4-isopropyl-di-benzoylmethane.

In a preferred embodiment of the presently claimed invention, the UV absorbing agents or sun screen agents are selected from the group consisting of 2-ethylhexyl-p-methoxycinnamate, 4,4'-t-butyl methoxydibenzoyl-methane, 2-hydroxy-4-methoxybenzophenone, octyldimethyl-p-aminobenzoic acid, digalloyltrioleate, 2,2-dihydroxy-4-methoxybenzophenone, ethyl-4(bis(hydroxypropyl)) aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, Methylene Bis-benzotriazolyltetramethylbutylphenol and mixtures thereof.

In an embodiment of the presently claimed invention, the thickening agents are selected from the group consisting of polymer thickening agents include non-ionic thickening agents and anionic thickening agents, or mixtures thereof. Suitable non-ionic thickening agents include polyacrylamide polymers, crosslinked poly(N-vinylpyrrolidones), polysaccharides, natural or synthetic gums or polysaccharides, polyvinylpyrrolidone, and polyvinylalcohol. Suitable anionic thickening agents include acrylic acid/ethyl acrylate copolymers, carboxyvinyl polymers and crosslinked copolymers of alkyl vinyl ethers and maleic anhydride.

In an embodiment of presently claimed invention, the thickening agents are selected from the group consisting of polysaccharides including cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof, natural gums like acacia, agar, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

In an embodiment of the presently claimed invention, the humectants are selected from the group consisting sodium 2-pyrrolidone-5-carboxylate (NaPCA), guanidine, glycolic acid and glycolate salts (e.g. ammonium and quaternary alkyl ammonium), lactic acid and lactate salts (e.g. ammonium and quaternary alkyl ammonium), aloe vera in any of its variety of forms (e.g., aloe vera gel), hyaluronic acid and derivatives thereof (e.g., salt derivatives such as sodium hyaluronate), lactamide monoethanolamine, acetamide monoethanolamine, urea, panthenol and derivatives thereof, and mixtures thereof.

In an embodiment of the presently claimed invention, the buffering agents are selected from the group consisting of Lactic acid, lactates, gluconic acid, glucono-delta-lactone, sodium gluconate and potassium gluconate, trisodium citrate, tripotassium citrate, sodium lactate and potassium lactate, In an embodiment of the presently claimed invention, the solvents are selected from the group consisting of Polyhydric alcohol include glycerin, diglycerin, triglycerin, polyglycerin, polypropylene glycol, polyethylene glycol, ethylene glycol, diethylene glycol, triethylene glycol, propylene glycol, dipropylene glycol, hexylene glycol, 1,3-butylene glycol, 1,4-butylene glycol, ethylene glycol monoalkyl ether, diethylene glycol monoalkyl ether, glucose, maltose, sucrose, lactose, xylitose, xylitol, sorbitol, mannitol, maltitol, malbit, panthenol, pentaerythritol, and hyaluronic acid and its salts, water, ethanol and isopropanol.

In an embodiment of the presently claimed invention, the solvents are selected from the group consisting of glycerin, water and ethanol.

In an embodiment of the presently claimed invention, the preservatives are selected from the group consisting of benzalkonium chloride, benzethonium chloride, benzyl alcohol, caprylyl glycol, chlorphenesin, 2,2'-dithiobis(N-methylbenzamide), diazolidinyl urea, ethylenediamine tetraacetic acid, ethylparaben, imidazolidinyl urea, methylparaben, phenoxyethanol, linoleamidopropyl PG-diammonium chloride phosphate, cocamidopropyl PG-diammonium chloride phosphate, propyl paraben, cis-1-(3-chloroallyl)-3,5,7-triaza-1-azoniaadamantane chloride, dehydroacetic acid or its salts, benzoic acid or its salts, sodium hydroxymethylglycinate and zinc pyrithione.

In an embodiment of the presently claimed invention, the liquid crystal lipid particles are included in a topical composition which further comprises sunscreen agents, UV absorbents, thickening agents and solvents.

In a preferred embodiment of the presently claimed invention, the liquid crystal lipid particles are included in a topical composition which further comprises diethylamino-hydroxybenzoylhexyl benzoate, ethylhexyl methoxycinnamate, acrylates/beheneth-25 methylacrylate copolymer, methylene Bis-benzotriazolyl tetramethylbutylphenol, decylglucoside, propylene glycol and Xanthan gum, ethanol, water and butylene glycol.

The effect of the present compositions in effecting barrier repair or maintaining the integrity of the skin's outer layer can be applied to a number of different uses. For example, the compositions can be used to treat any condition in which a deficient or faulty barrier is a factor. In this regard, the compositions can be used to improve the long term moisture retention of the skin, or in prevention or treatment of dry skin conditions generally, or specific dry skin conditions, such as result from regular exposure to detergents, soaps and hot water; seasonal exposure to harsh weather conditions, e.g., cold, wind and/or sun; occupational exposure to harsh chemicals or other drying or damaging agents; or pathological conditions such as eczematous dermatitis, psoriasis, ichthyoses, xerosis and the like.

It is also well-known that dry skin is commonly associated with aging (both intrinsic and photoaging), and the compositions can be used in prevention of further damage to aging skin, or treatment and/or reversal of already present damage, including the appearance of fine lines and wrinkles, which, are frequently associated with dry skin and the thinning of the stratum corneum that occurs with age. The compositions can also be used in the treatment of a defective skin barrier, such, as occurs on the soles of the feet, and palms of the hands, where the stratum corneum is very thick, but the lipid barrier is poor. In addition, defective skin barriers frequently occur in association with burns, wounds, blisters, stasis ulcers and bedsores; such injuries can be expected to benefit from application of the compositions.

The compositions of the invention can be used for the reduction of the skin's response to irritants and sensitizers. A significant percentage of the population has sensitive skin, in that they perceive a frequent, stinging or painful response to various elements to which the skin may be exposed, be it through makeup or skin care products, environmental stimuli such as smoke or pollution, or occupational exposure to chemicals. In addition, even normal skin can have a reaction to exposure to known irritants, such as acids.

As it is well known that the stratum corneum and lipids constitute the first line of defense against irritants, by providing a physical barrier to permeability of such materials to the lower skin layers, the application of the compositions of the invention, by increasing the integrity of the barrier, can reduce the reactivity of the skin of both normal and sensitive individuals to irritants and sensitizers, in one embodiment, for example, the compositions can be used to reduce the reaction of the skin to the irritation caused by therapeutic acids such as alpha- and beta-hydroxy acids, retinoic acid, and the like, or to reduce the irritation caused by insect bites or stings, or alleviate the irritation experienced with contact dermatitis.

The compositions of the invention are employed in a manner that is appropriate to the intended final use of the product. For example, in the treatment of occasional dry skin due to exposure to weather or other temporary conditions, or in the treatment of occasional skin irritation, the compositions can be used on an as-needed basis until the condition is relieved. When being used to treat a more permanent condition, for example, a condition associated with a defective or deficient lipid barrier, particularly sensitive skin, dry skin associated with any type of aging, or the wrinkling or fine lines associated with a thinning of the stratum corneum with aging, the composition, is preferably applied chronically, to prevent recurrence of the condition.

In an embodiment, the composition of the presently claimed invention can be applied in an amount of from about 0.1 mg/cm$^2$ to 2 mg/cm$^2$ of skin, from about once per week to about 4 or 5 times daily, preferably from about 3 times a week to about 3 times daily, most preferably about once or twice per day.

Further the composition of the presently claimed invention may be applied for longer duration preferably for a period of at least about one month, from about three months to about twenty years, more preferably from about six months to about ten years, more preferably still from about one year to about five years, thereby resulting in the treatment or prevention of the condition in question.

Advantages

1. The liquid crystal lipid particles are of definite shape and thereby they mimic the skin structure.
2. The liquid crystal lipid particles containing compositions form flexible films on the skin and thus the skin could be protected from pollutants and it has a moisturizing effect on the skin.
3. The liquid crystal lipid particles compositions are stable at varied temperature conditions.

EMBODIMENTS

1. A method for reducing the adhesion of dust to skin comprising applying to the skin at least one liquid crystal lipid particle
   wherein the liquid crystal lipid particles comprises compounds represented by the general formulae (I) to (VI), comprising,
   at least one compound of formula (I)

general formula (I)

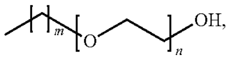

wherein m is an in the range from ≥10 to ≤24 and n is an integer in the range from ≥1 to ≤25, at least one compound of formula (II)

general formula (II)

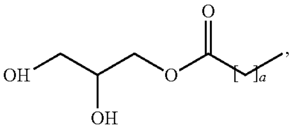

wherein a is an in the range from ≥10 to ≤24, at least one compound of formula (III)

general formula (III)

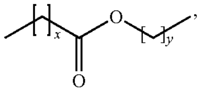

wherein x is an in the range from ≥10 to ≤24 and y is an integer in the range from ≥10 to ≤25, at least one compound of formula (IV)

general formula (IV)

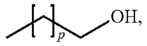

wherein p is an in the range from ≥10 to ≤16, at least one compound of formula (V)

general formula (V)

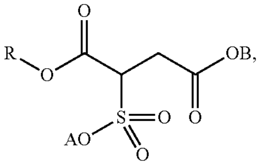

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

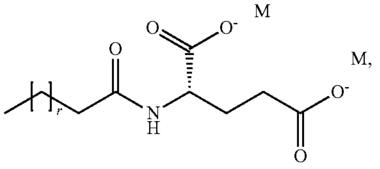

wherein r is an in the range from ≥9 to ≤18, and M is a hydrogen atom, an alkali earth metal or an alkaline earth metal.

2. Use of at least one liquid crystal lipid particle for reducing the adhesion of dust to the skin, wherein the liquid crystal lipid particles comprise compounds represented by the general formulae (I) to (VI), comprising,
   at least one compound of formula (I)

general formula (I)

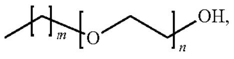

wherein m is an in the range from ≥10 to ≤24 and n is an integer in the range from ≥1 to ≤25, at least one compound of formula (II)

general formula (II)

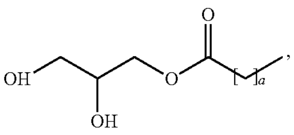

wherein a is an in the range from ≥10 to ≤24, at least one compound of formula (III)

general formula (III)

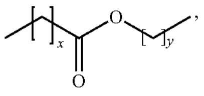

wherein x is an in the range from ≥10 to ≤24 and y is an integer in the range from ≥10 to ≤25, at least one compound of formula (IV)

general formula (IV)

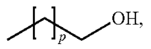

wherein p is an in the range from ≥10 to ≤16, at least one compound of formula (V)

general formula (V)

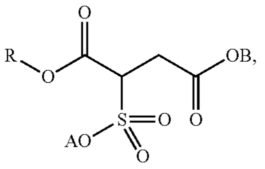

wherein A and B are each independently a hydrogen atom or alkali earth metal or an alkaline earth metal, and R is a linear or branched, saturated or unsaturated $C_{10}$-$C_{20}$ aliphatic radical and at least one compound of formula (VI)

general formula (VI)

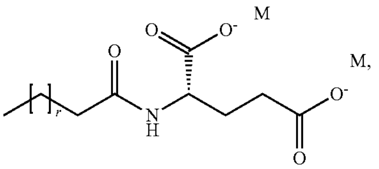

wherein r is an in the range from ≥9 to ≤18, and M is a hydrogen atom, an alkali earth metal or an alkaline earth metal.

3. The method or use according to embodiment 1 or 2, wherein the liquid crystal lipid particles have a lamellar structure with orthorhombic lateral packing.
4. The method or use according to embodiment 1 or 2, wherein the liquid crystal lipid particles have an average particle size in the range of ≥20 nm to ≤300 nm, determined using dynamic light scattering using Malvern DLS ZS90.
5. The method or use according to embodiment 1 or 2, wherein the liquid crystal lipid particles have a zeta potential is more than 20 mV.
6. The method or use according to embodiments 1 to 5, wherein the at least one compound of general formula (I) is selected from the group consisting of ceteareths, polyoxyethylene stearyl ether, and polyoxyethylene cetyl ether.
7. The method or use according to embodiments 1 to 6, wherein the at least one compound of general formula (II) is selected from the group consisting of glycerol stearate, glycerol laurate and glycerol palmitate.
8. The method or use according to embodiments 1 to 7, wherein the at least one compound of general formula (III) is selected from the group consisting of cetyl palmitate, myristyl myristate, tetra decyl tetra decanoate, and behenyl behenate.
9. The method or use according to embodiments 1 to 8, wherein the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol, stearyl alcohol or mixtures thereof.
10. The method or use according to embodiments 1 to 9, wherein the at least one compound of general formula (V) is disodium $C_{10}$-$C_{18}$ alkyl sulfosuccinate.
11. The method or use according to embodiments 1 to 10, wherein the at least one compound of general formula (VI) is selected from the group consisting of sodium lauroyl glutamate, sodium cocoyl glutamate, sodium myristoyl glutamate and sodium steraroyl glutamate.
12. The method or use according to one or more of embodiments 1 to 11, wherein the liquid crystal lipid particles comprise ceteareths, glycerol stearate, cetyl palmitate, cetyl alcohol and stearyl alcohol.
13. The use according to one or more of embodiments 1 to 11, wherein the liquid crystal lipid particles comprise ceteareths, glycerol stearate, cetyl palmitate, myristyl myristate, cetyl alcohol and stearyl alcohol.
14. The use according to one or more of embodiments 1 to 11, wherein the liquid crystal lipid particles comprise ceteareths, glycerol stearate, cetyl palmitate, myristyl myristate, cetyl alcohol, stearyl alcohol and a compound selected from the group of disodium $C_{10}$-$C_{18}$ alkyl sulfosuccinate and sodium steraroyl glutamate.
15. The use according to one or more of embodiments 1 to 11, wherein the liquid crystal lipid particles comprise ceteareth-12, ceteareth-12, glycerol stearate, cetyl palmitate, myristyl myristate, cetyl alcohol, stearyl alcohol and a compound selected from the group of disodium $C_{16}$-$C_{18}$ alkyl sulfosuccinate and sodium steraroyl glutamate.
16. A topical composition comprising,
    at least one liquid crystal particle as defined in one or more of embodiments 1 to 15,
    at least one thickening agent and
    water.
17. The topical composition according to embodiment 16, wherein the at least one thickening agent is selected from the group consisting of xanthan gum, succinoglycan, gellan gum, pectin, alginates, starches, guars, acrylates, acrylate copolymers, carbomers and associative thickeners.
18. The topical composition according to embodiments 16 or 17, wherein the at least one liquid crystal lipid particle is present in an amount in the range of % to 30% by weight, based on the total weight of the topical composition.
19. The topical composition according to one or more of embodiments 16 to 18, wherein the at least one thickening agent is present in an amount in the range of % to 5% by weight, based on the total weight of the topical composition.
20. The topical composition according to one or more of embodiments 16 to 19, wherein water is present in an amount in the range of % to 80% by weight, based on the total weight of the topical composition.
21. The topical composition according to one or more of embodiments 16 to 20, which further comprises at least one auxiliary agent selected form the group consisting of anti-wrinkle active agents, anti-acne active agents, emulsifiers antioxidants, emollients, self-tanning active agents, skin lightening agents, sunscreen agents, humectants, abrasives, absorbents, fragrances, buffering agents, opacifying agents, colorants, preservatives, fillers and pH adjusting agents.

22. The topical composition according to one or more of embodiments 16 to 21, wherein the topical composition is a skin care composition.
23. The topical composition according to one or more of embodiments 12 to 22, wherein the topical composition is present in the form of a cream, a foam, a lotion, a gel, a paste or an ointment.
24. A method for reducing the adhesion of dust to skin comprising applying to the skin the topical composition according to one or more of embodiments 16 to 23.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the presently claimed invention, which are apparent to one skilled in the art.

Materials

Materials from BASF:

- Emulgade® SE-PF is glyceryl stearate, ceteareth-20, ceteareth-12, cetyl alcohol, cetyl palmitate is an emulsifying base.
- Eumulgin® B1 is ceteareth-12 (cetyl stearyl alcohol with 12 mol EO) which is a non-ionic emulsifier
- Cetiol® MM is myristyl myristate which is an emollient
- Eumulgin® Prisma is disodium C16-C18 alkyl sulfosuccinate which is an anionic emulsifier
- Eumulgin® SG is sodium stearoyl glutamate which is an anionic emulsifier.
- Uvinul® A Plus is diethylamino hydroxybenzoyl hexyl benzoate which is a UV absorber
- Uvinul® MC 80 is ethylhexyl methoxycinnamate which is a UV absorber
- Tinovis® GTC is acrylates/beheneth-25 methylacrylate copolymer is a thickening agent or a viscosity modifier
- Rhenocare® XGN is xanthan gum which is a thickening agent or viscosity modifier.
- Tinisorb® M is methylene bis-benzotriazolyl tetramethylbutylphenol, water, decylglucoside, propylene glycol and xanthan gum which is a UV filter From Clariant

- Phenonip® is phenoxyethanol (and) methylparaben (and) ethylparaben (and) propylparaben (and) butylparaben (and) isobutylparaben which is used as a broad spectrum antimicrobial agent or preservative

Methods

Measurement of particle size: Particle size measurement of the liquid crystal lipid particles was done using Malvern DLS ZS90.

Measurement of zeta potential: Zeta potential was measured using Zetasizer nano ZS90 (Malvern)

Example 1

Base Composition of the Liquid Crystal Lipid Particles

| Part | Ingredient | Ex. 1B1 (% w/w) | Ex. 1B2 (% w/w) | Ex. 1B3 (% w/w) | Ex. 1B4 (% w/w) | Ex. 1B5 (% w/w) | Ex. 1B6 (% w/w) |
|---|---|---|---|---|---|---|---|
| A | Emulgade ® SE-PF | 7.50 | 7.50 | 7.50 | 7.50 | 7.50 | 7.50 |
| | Eumulgin ®B1 | 7.50 | 7.50 | 7.50 | 7.50 | 7.50 | 7.50 |
| | Cetiol ® MM | 15.00 | 15.00 | 15.00 | 15.00 | 15.00 | 15.00 |
| B | Water | 29.00 | 29.00 | 29.00 | 28.90 | 28.80 | 28.70 |
| | Eumulgin ® Prisma | — | 0.10 | 0.20 | — | — | — |
| | Eumulgin ® SG | — | — | — | 0.10 | 0.20 | 0.30 |
| C | Water | 10.00 | 10.00 | 10.00 | 10.00 | 10.00 | 10.00 |
| | Glycerin | 20.00 | 20.00 | 20.00 | 20.00 | 20.00 | 20.00 |
| D | Water | 10.00 | 10.00 | 10.00 | 10.00 | 10.00 | 10.00 |
| | preservative | q.s. | q.s. | q.s. | q.s. | q.s. | q.s. |

q.s. = quantity sufficient

Process of manufacture: Phase inversion temperature emulsification method

1) Ingredients of part A and part B were and heated separately to 80° C.
2) Part A was added to part B and was mixed until it was homogenous to form the base using a homogenizer.
3) Part C was mixed to the base of step 2.
4) The base formed in step 4 was cooled down to room temperature in an ice bath.
5) Part D was added to the base and was mixed until homogenous using a homogenizer.

Results

| Results | Ex. 1B1 | Ex. 1B2 | Ex. 1B3 | Ex. 1B4 | Ex. 1B5 | Ex. 1B6 |
|---|---|---|---|---|---|---|
| Appearance | Translucent | Translucent | Translucent | Translucent | Translucent | translucent |
| Stability (RT) | Stable | Stable | Stable | Stable | Stable | Stable |
| Stability (50° C.) | Unstable | Unstable | Stable | Unstable | Stable | Stable |
| Stability (−20° C.) | Stable | Stable | Stable | Stable | Stable | Stable |
| Zeta potential (mV) | −1.8 | −17.3 | −21.9 | −18.9 | −23.1 | −24.9 |

Example 2

| Part | Ingredient | Ex. 2T1 (% w/w) | Ex. 2T2 (% w/w) | Ex. 2T3 (% w/w) |
|---|---|---|---|---|
| A | Uvinul ® A Plus | 4 | 4 | 4 |
| | Univul ® MC 80 | 10 | 10 | 10 |
| B | Water | to 100 | To 100 | To 100 |
| | Butylene glycol | 2.5 | 2.5 | 2.5 |
| | Tinovis ® GTC | 1.5 | 1.5 | 1.5 |
| C | Sodium hydroxide (20% solution) | To pH 7.0 | To pH 7.0 | To pH 7.0 |
| D | Tinosorb ® M | 5 | 5 | 5 |
| | Ethanol | 5 | 5 | 5 |
| | Water | 5 | — | — |
| | Base of liquid crystal lipid particles (Ex 1. B5) | — | 5 | — |
| | Base of macroparticle by conventional method | — | — | 5 |

Process of Manufacture:—

1) Ingredients of part A and part B were and heated separately to 80° C.
2) Part A was added to part B under homogenization and was mixed until it was homogenous.
3) Part C was mixed with the mixture of part A and B and cool down to 45° C.
4) Part D was added to the mixture of step 3 and was mixed until homogenous using a homogenizer. This was then cooled down to room temperature.

Example 3

Anti-Dust Performance—Test Protocol 1) 4 g of the compositions according to Examples 2T1 to 2T3 were each applied on the PMMA boards.
2) 2 g of the composition was further applied on the boards to ensure uniform distribution of the composition on the board.
3) The boards were placed in an oven at 38° C. overnight
4) Placed the board on the dish having weighted amount of dust in an upside down manner and gently shake for 30 sec.
5) Turned over the board back again and weighed the dishes for the sand.

Results

| Dust adhesion | Ex. 3T1 | Ex. 3T2 | Ex. 3T3 |
|---|---|---|---|
| | 33% | 22% | 27% |

The lower dust adhesion in Example 3T2 indicates the superior performance of the composition comprising liquid crystal lipid particles as the base.

Refer FIGS. 3 and 4 indicate the reduction in the dust adhesion on the skin surface after application of the composition comprising liquid crystal lipid particles.

Example 4

To Test the Moisturizing Effect

| Part | Ingredient | Ex. 4T4 (% w/w) | Ex. 4T5 (% w/w) |
|---|---|---|---|
| A | Water | 88.30 | 88.30 |
| | Rheocare ® XGN | 1.00 | 1.00 |
| | Eumulgin ® Prisma | 0.20 | 0.20 |
| | Phenonip ® | 0.50 | 0.50 |
| B | Water | 8.00 | — |
| | Glycerin | 2.00 | |
| | Base of Liquid crystal lipid particles (Ex. 1B5) | | 10.00 |

Process of Manufacture—

1) Dissolve part A at 80° C.
2) Cool down the base to room temperature, then add part B into the base. Mix until homogenous.

Results: The composition of example 4T5 showed a threefold increase in the moisturizing effect as compared to example 4T4 when measured on the corneometer. FIG. 5 indicates the results of example 4T4.

The invention claimed is:

1. A method for reducing adhesion of dust, the method comprising applying a topical cosmetic composition comprising at least one liquid crystal lipid particle, at least one thickening agent in the range of 0.1% to 5% by weight, based on the total weight of the topical composition, and water in the range of 5% to 80% by weight, based on the total weight of the topical composition, wherein the at least one liquid crystal lipid particle is made using a phase inversion temperature method, and consists of compounds represented by general formulae (I) to (VI) as follows:

at least one compound of formula (I)

general formula (I)

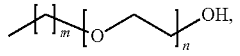

wherein m is an integer in the range from ≥10 to ≤24 and n is an integer in the range from ≥1 to ≤25, at least one compound of formula (II)

general formula (II)

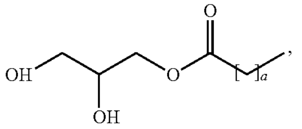

wherein a is an integer in the range from ≥10 to ≤24, at least one compound of formula (III)

general formula (III)

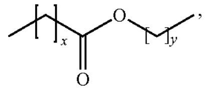

wherein x is an integer in the range from ≥10 to ≤24 and y is an integer in the range from ≥10 to ≤25, at least one compound of formula (IV)

general formula (IV)

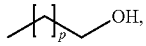

wherein p is an in the range from ≥10 to ≤16, at least one compound of formula (V)

general formula (V)

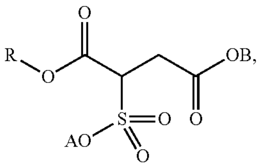

wherein A and B are each independently a hydrogen atom or alkali metal or an alkaline earth metal, and R is a linear or branched, saturated or unsaturated $C_{10}$-$C_{20}$ aliphatic radical and at least one compound of formula (VI)

general formula (VI)

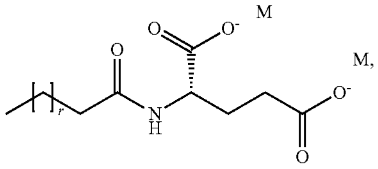

wherein r is an integer in the range from ≥9 to ≤18, and M is a hydrogen atom, an alkali metal or an alkaline earth metal, and optionally preservatives, and wherein the at least one liquid crystal lipid particles have a zeta potential of more than 20 mV.

2. The method according to claim 1, wherein the at least one liquid crystal lipid particle has a lamellar structure with orthorhombic lateral packing.

3. The method according to claim 1, wherein the at least one liquid crystal lipid particle has an average particle size in the range of ≥20 nm to ≤300 nm, determined using dynamic light scattering using Malvern DLS ZS90.

4. The method according to claim 1, wherein the at least one compound of general formula (I) is selected from the group consisting of ceteareths, polyoxyethylene stearyl ether, and polyoxyethylene cetyl ether.

5. The method according to claim 1, wherein the at least one compound of general formula (II) is selected from the group consisting of glycerol stearate, glycerol laurate and glycerol palmitate.

6. The method according to claim 1, wherein the at least one compound of general formula (III) is selected from the group consisting of cetyl palmitate, myristyl myristate, tetra decyl tetra decanoate, and behenyl behenate.

7. The method according to claim 1, wherein the at least one compound of general formula (IV) is selected from the group consisting of lauryl alcohol, tridecyl alcohol, myristyl alcohol, pentadecyl alcohol, cetyl alcohol, palmitoleyl alcohol, heptadecyl alcohol, stearyl alcohol or mixtures thereof.

8. The method according to claim 1, wherein the at least one compound of general formula (V) is disodium $C_{10}$-$C_{18}$ alkyl sulfosuccinate.

9. The method according to claim 1, wherein the at least one compound of general formula (VI) is selected from the group consisting of sodium lauroyl glutamate, sodium cocoyl glutamate, sodium myristoyl glutamate and sodium steraroyl glutamate.

10. The method according to claim 1, wherein the at least one liquid crystal lipid particle consists of ceteareths, glycerol stearate, cetyl palmitate, myristyl myristate, cetyl alcohol, stearyl alcohol, disodium $C_{10}$-$C_{18}$ alkyl sulfosuccinate and sodium steraroyl glutamate.

11. The method according to claim 1, wherein the at least one liquid crystal lipid particle consists of ceteareth-20, ceteareth-12, glycerol stearate, cetyl palmitate, myristyl myristate, cetyl alcohol, stearyl alcohol, disodium $C_{16}$-$C_{18}$ alkyl sulfosuccinate and sodium steraroyl glutamate.

12. The method according to claim 1, wherein the at least one thickening agent is selected from the group consisting of xanthan gum, succinoglycan, gellan gum, pectin, alginates, starches, guars, acrylates, acrylate copolymers, carbomers and associative thickeners.

13. The method according to claim 1, wherein the at least one liquid crystal lipid particle is present in an amount in the range of ≥1% to ≤30% by weight, based on the total weight of the topical composition.

14. The method according to claim 1, wherein the topical composition further comprises at least one auxiliary agent selected from the group consisting of anti-wrinkle active agents, anti-acne active agents, emulsifiers, antioxidants, emollients, self-tanning active agents, skin lightening agents, sunscreen agents, humectants, abrasives, absorbents, fragrances, buffering agents, opacifying agents, colorants, preservatives, fillers and pH adjusting agent.

15. The method according to claim 1, wherein the topical composition is a skin care composition.

16. The method according to claim 1, wherein the topical composition is present in the form of a cream, a foam, a lotion, a gel, a paste or an ointment.

* * * * *